(12) United States Patent
Perkins et al.

(10) Patent No.: US 10,933,178 B2
(45) Date of Patent: Mar. 2, 2021

(54) LEAK-RESISTANT BANDAGE SYSTEMS AND METHODS WITH HYDROPHILIC FOAM WOUND INSERT FOR FLUID-INSTILLATION AND/OR NEGATIVE-PRESSURE WOUND THERAPIES

(71) Applicant: KCI Licensing, Inc., San Antonio, TX (US)

(72) Inventors: Joanna Payne Perkins, San Antonio, TX (US); Paul S. Slack, San Jose, CA (US); Kevin Higley, San Antonio, TX (US); Kenneth Mitchel Knowles, Bandera, TX (US); Aidan Marcus Tout, Alderbury (GB)

(73) Assignee: KCI Licensing, Inc., San Antonio, TX (US)

( * ) Notice: Subject to any disclaimer, the term of this patent is extended or adjusted under 35 U.S.C. 154(b) by 385 days.

(21) Appl. No.: 16/002,155

(22) Filed: Jun. 7, 2018

(65) Prior Publication Data

US 2018/0280595 A1    Oct. 4, 2018

Related U.S. Application Data

(60) Division of application No. 14/572,158, filed on Dec. 16, 2014, now Pat. No. 10,016,541, which is a
(Continued)

(51) Int. Cl.
*A61M 1/00* (2006.01)
*A61F 13/02* (2006.01)
(Continued)

(52) U.S. Cl.
CPC ........... *A61M 1/0084* (2013.01); *A61F 13/02* (2013.01); *A61F 13/022* (2013.01);
(Continued)

(58) Field of Classification Search
CPC ... A61M 1/0084; A61F 13/02; A61F 13/0216; A61F 13/022; A61F 13/0266
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

Extended European Search Report for corresponding Application No. 181732207, dated Jul. 9, 2018.
(Continued)

*Primary Examiner* — Nicholas J. Weiss
*Assistant Examiner* — Gabriella E Burnette

(57) ABSTRACT

Wound treatment systems and methods (e.g., having hydrophilic wound inserts), such as for negative-pressure and/or fluid-installation wound therapies. Some embodiments include a check-valve assembly between a wound dressing and a vacuum source.

12 Claims, 6 Drawing Sheets

Related U.S. Application Data continuation of application No. 13/009,116, filed on Jan. 19, 2011, now Pat. No. 9,089,630.

(60) Provisional application No. 61/296,822, filed on Jan. 20, 2010.

(51) Int. Cl.
  *F16K 15/00* (2006.01)
  *A61F 13/00* (2006.01)

(52) U.S. Cl.
  CPC ...... *A61F 13/0216* (2013.01); *A61F 13/0266* (2013.01); *A61M 1/0031* (2013.01); *A61M 1/0088* (2013.01); *F16K 15/00* (2013.01); *A61F 2013/0028* (2013.01); *A61F 2013/00174* (2013.01); *A61F 2013/00536* (2013.01)

(56) References Cited

U.S. PATENT DOCUMENTS

| | | | |
|---|---|---|---|
| 2,632,443 A | 3/1953 | Lesher | |
| 2,682,873 A * | 7/1954 | Evans | A61F 13/00029 |
| | | | 602/42 |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A * | 11/1980 | Lock | A61F 13/00017 |
| | | | 521/51 |
| 4,245,630 A | 1/1981 | Lloyd et al. | |
| 4,256,109 A * | 3/1981 | Nichols | A61M 1/005 |
| | | | 137/202 |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A * | 6/1985 | Vaillancourt | B01D 67/0088 |
| | | | 210/500.36 |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A * | 5/1987 | Webster | A61F 13/00063 |
| | | | 602/47 |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A * | 11/1988 | Fox | A61K 41/0047 |
| | | | 601/2 |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,957,810 A * | 9/1990 | Eleouet | A47L 13/17 |
| | | | 428/306.6 |
| 4,969,880 A | 11/1990 | Zamierowski | |
| 4,985,019 A | 1/1991 | Michelson | |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A * | 12/1992 | Karami | A61F 13/0203 |
| | | | 602/42 |
| 5,176,663 A | 1/1993 | Svedman et al. | |
| 5,215,522 A * | 6/1993 | Page | A61M 16/0463 |
| | | | 128/207.16 |
| 5,232,453 A | 8/1993 | Plass et al. | |
| 5,261,893 A | 11/1993 | Zamierowski | |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,490,503 A | 2/1996 | Hollister | |
| 5,527,293 A * | 6/1996 | Zamierowski | A61F 5/453 |
| | | | 128/898 |
| 5,549,584 A | 8/1996 | Gross | |
| 5,556,375 A | 9/1996 | Ewall | |
| 5,607,388 A | 3/1997 | Ewall | |
| 5,636,643 A * | 6/1997 | Argenta | A61M 1/0088 |
| | | | 128/897 |
| 5,645,081 A | 7/1997 | Argenta et al. | |
| 5,720,325 A * | 2/1998 | Grantham | B67D 7/0478 |
| | | | 138/113 |
| 5,960,822 A | 10/1999 | Matuschka et al. | |
| 5,971,353 A | 10/1999 | Johnson | |
| 6,071,267 A * | 6/2000 | Zamierowski | A61F 13/0203 |
| | | | 604/289 |
| 6,135,116 A | 10/2000 | Vogel et al. | |
| 6,168,400 B1 * | 1/2001 | Van Davelaar | F16K 17/18 |
| | | | 137/454.2 |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 7,438,705 B2 | 10/2008 | Karpowicz et al. | |
| 7,651,484 B2 | 1/2010 | Heaton et al. | |
| 7,846,141 B2 | 12/2010 | Weston | |
| 8,057,443 B2 | 11/2011 | McNeil | |
| 8,062,273 B2 | 11/2011 | Weston | |
| 8,172,555 B2 | 5/2012 | Reynolds | |
| 8,216,198 B2 | 7/2012 | Heagle et al. | |
| 8,251,979 B2 | 8/2012 | Malhi | |
| 8,257,327 B2 | 9/2012 | Blott et al. | |
| 8,398,614 B2 | 3/2013 | Blott et al. | |
| 8,449,509 B2 | 5/2013 | Weston | |
| 8,529,548 B2 | 9/2013 | Blott et al. | |
| 8,535,296 B2 | 9/2013 | Blott et al. | |
| 8,551,060 B2 | 10/2013 | Schuessler et al. | |

(56) References Cited

U.S. PATENT DOCUMENTS

| | | | |
|---|---|---|---|
| 8,568,386 B2 | 10/2013 | Malhi | |
| 8,679,081 B2 | 3/2014 | Heagle et al. | |
| 8,834,451 B2 | 9/2014 | Blott et al. | |
| 8,926,592 B2 | 1/2015 | Blott et al. | |
| 9,017,302 B2 | 4/2015 | Vitaris et al. | |
| 9,089,630 B2 * | 7/2015 | Perkins | A61M 1/0088 |
| 9,198,801 B2 | 12/2015 | Weston | |
| 9,211,365 B2 | 12/2015 | Weston | |
| 9,289,542 B2 | 3/2016 | Blott et al. | |
| 2002/0007157 A1 * | 1/2002 | Azzolini | A61M 39/24 |
| | | | 604/247 |
| 2002/0077661 A1 | 6/2002 | Saadat | |
| 2002/0115951 A1 | 8/2002 | Norstrem et al. | |
| 2002/0120185 A1 | 8/2002 | Johnson | |
| 2002/0143286 A1 | 10/2002 | Tumey | |
| 2002/0183702 A1 | 12/2002 | Henley et al. | |
| 2003/0140794 A1 * | 7/2003 | Wang | B01D 39/1676 |
| | | | 96/226 |
| 2004/0030322 A1 | 2/2004 | Phung et al. | |
| 2004/0211468 A1 * | 10/2004 | Horton | F16K 15/147 |
| | | | 137/511 |
| 2005/0256461 A1 * | 11/2005 | DiFiore | A61M 39/105 |
| | | | 604/247 |
| 2006/0122536 A1 | 6/2006 | Haar et al. | |
| 2007/0167926 A1 * | 7/2007 | Blott | A61M 1/0088 |
| | | | 604/304 |
| 2009/0036873 A1 * | 2/2009 | Nielsen | A61M 1/0072 |
| | | | 604/543 |
| 2009/0125004 A1 * | 5/2009 | Shen | A61M 1/0068 |
| | | | 604/543 |
| 2009/0221990 A1 * | 9/2009 | Jaeb | A61M 1/0001 |
| | | | 604/540 |
| 2009/0227969 A1 * | 9/2009 | Jaeb | A61M 1/0049 |
| | | | 604/313 |
| 2009/0281526 A1 * | 11/2009 | Kenny | A61M 1/0086 |
| | | | 604/543 |
| 2009/0306630 A1 * | 12/2009 | Locke | A61M 1/0001 |
| | | | 604/543 |
| 2010/0286596 A1 * | 11/2010 | Hofmann | A61M 39/105 |
| | | | 604/35 |
| 2011/0117208 A1 | 5/2011 | Richardson et al. | |
| 2011/0190735 A1 | 8/2011 | Locke et al. | |
| 2012/0316538 A1 | 12/2012 | Heiser et al. | |
| 2014/0163491 A1 | 6/2014 | Schuessler et al. | |
| 2015/0080788 A1 | 3/2015 | Blott et al. | |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 9704258 A1 | 2/1997 |
| WO | 97/18007 A1 | 5/1997 |
| WO | 99/13793 A1 | 3/1999 |

OTHER PUBLICATIONS

European Examination Report for Corresponding Application No. 181732207, dated Sep. 30, 2019.

Louis C. Argenta, MD and Michael J. Morykwas, PhD; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

(56) References Cited

OTHER PUBLICATIONS

Chinn, Steven D. et al: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

European Search Report for EP11735080 dated May 29, 2013.

* cited by examiner

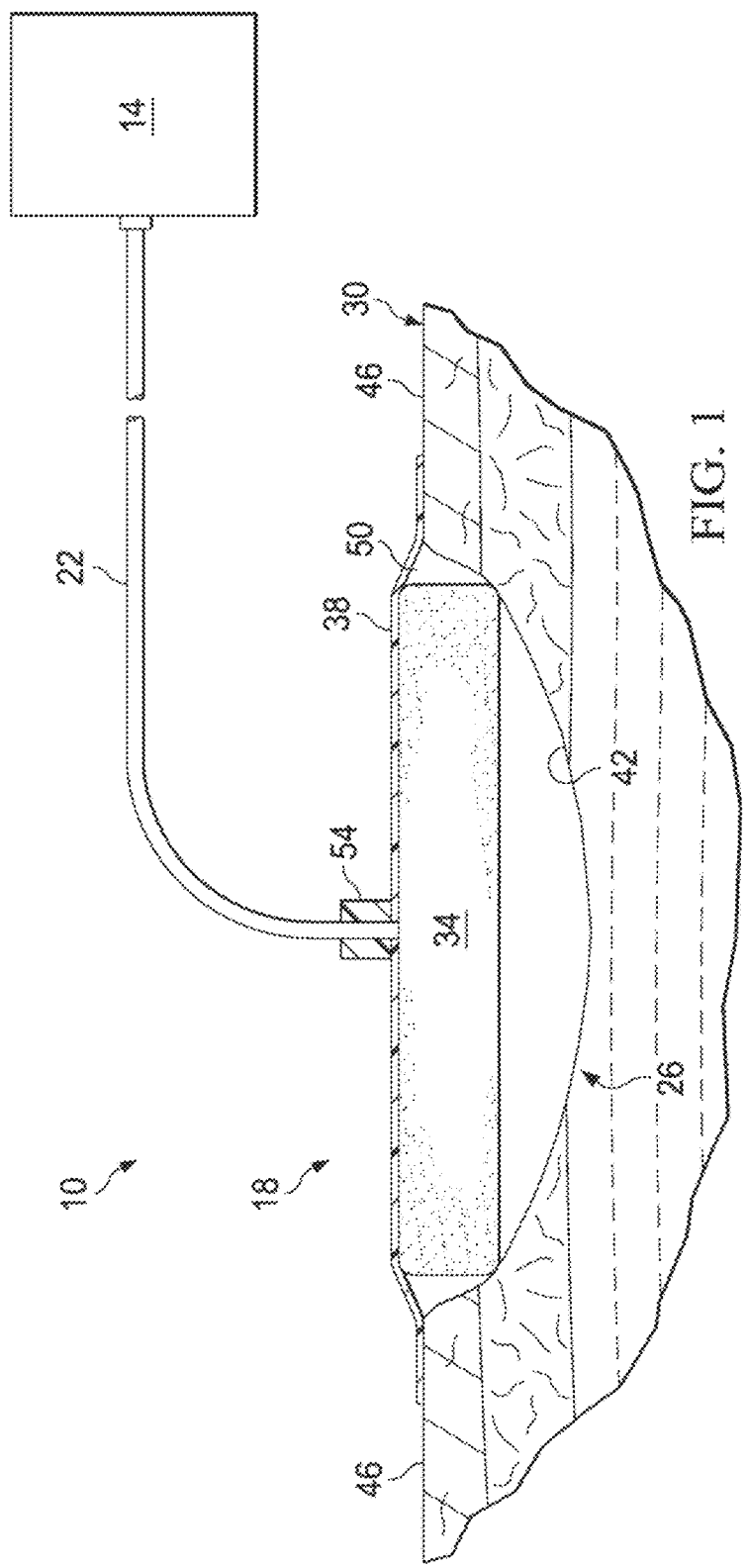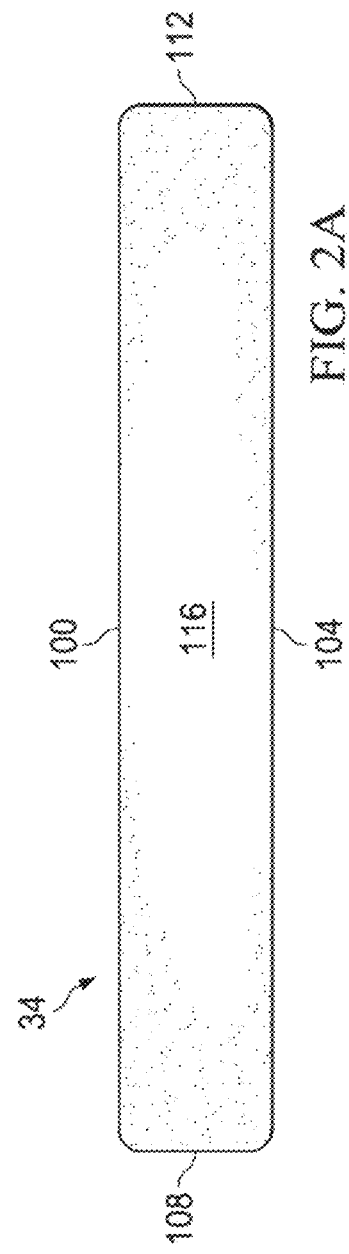

LEAK-RESISTANT BANDAGE SYSTEMS AND METHODS WITH HYDROPHILIC FOAM WOUND INSERT FOR FLUID-INSTILLATION AND/OR NEGATIVE-PRESSURE WOUND THERAPIES

CROSS-REFERENCE TO RELATED APPLICATIONS

This application is a divisional of U.S. patent application Ser. No. 14/572,158, filed Dec. 16, 2014 which is a continuation of U.S. patent application Ser. No. 13/009,116, filed Jan. 19, 2011, now U.S. Pat. No. 9,089,630 which claims priority to U.S. Provisional Patent Application No. 61/296,822, filed Jan. 20, 2010, the contents of each of which is incorporated herein in their entirety.

BACKGROUND

1. Field of the Invention

The present invention relates generally to healing of wounds and wound-treatment therapies. More particularly, but not by way of limitation, the present invention relates to fluid-instillation and negative-pressure wound therapies.

2. Background Information

Clinical studies and practice have shown that providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a wound insert (e.g., a porous pad or other manifold device). The wound insert typically contains cells or pores that are capable of distributing reduced pressure to the tissue and channeling fluids that are drawn from the tissue. The wound insert can be incorporated into a wound dressing having other components that facilitate treatment, such as, for example, a drape (e.g., adhesive surgical drape). Instillation of fluids (e.g., irrigation fluids and/or medicaments) may be used in conjunction with negative pressure wound therapy to promote healing and/or improve efficacy.

While NPWT has been highly successful in the promotion of wound closure, healing many wounds previously thought largely untreatable, some difficulty remains. With current negative-pressure and/or fluid-instillation systems, leaks may occur at the dressing site due to the presence of fluid (e.g., instillation fluids, body fluids, etc.) and/or due to such fluids being forced to the perimeter of a wound insert (e.g., a foam wound insert). Such fluids may interact with the adhesive between the drape and adjacent healthy skin, and can lead to failure and leakage, thus requiring removal of a wound dressing and application of a new dressing. Such removal and re-application can be detrimental to a patient as the wound is exposed to external atmosphere (e.g., bacteria, contaminants, and the like). Further, fluid forced to the edges of wound can pool and/or macerate/damage the periwound skin and/or intact skin.

SUMMARY

The present disclosure includes embodiments of methods of forming a wound insert, wound-treatment methods, wound dressings, and wound-treatment systems.

Some embodiments of the present check-valve assemblies comprise: a housing defining a first connection, a second connection, a first passageway between the first and second connections, and a second passageway between the first and second connections that is distinct from the first passageway; a check valve disposed in the first passageway and configured to: permit fluid to pass through the check valve assembly from the first connection to the second connection if the pressure at the second connection is less than the pressure at the first connection; and substantially prevent fluid from passing through the check valve from the second connection to the first connection if the pressure at the second connection is greater than the pressure at the first connection. In some embodiments, the check valve comprises a duckbill valve. In some embodiments, the check valve comprises a ball valve. In some embodiments, the first connection comprises a multi-lumen connection having a first lumen in communication with the first passageway, and a second lumen in communication with the second passageway, and where the second connection comprises a multi-lumen connection having a first lumen in communication with the first passageway, and a second lumen in communication with the second passageway. In some embodiments, the second lumen of the first connection is an annular lumen disposed around the first lumen of the first connection, and where the second lumen of the second connection is an annular lumen disposed around the first lumen of the second connection.

Some embodiments of the present wound-treatment systems comprise: a fluid source configured to be coupled to a wound dressing such that the fluid source is actuatable to deliver a fluid to the wound dressing; a check-valve assembly configured to be coupled to a wound dressing; a vacuum source configured to be coupled to the check-valve assembly such that the vacuum source is actuatable to apply negative pressure to a wound dressing through the check-valve assembly; where the system is configured such that (e.g., if a wound dressing is coupled to the fluid source, the vacuum source, and the check-valve assembly, and the wound dressing is coupled to skin adjacent a wound of a patient such that the wound dressing covers the wound to form a substantially enclosed space adjacent the wound) the check-valve assembly: substantially prevents fluid flow through the check-valve assembly toward the wound dressing. In some embodiments, the system can be configured such that the check-valve assembly substantially prevents pressure in the space adjacent the wound from exceeding atmospheric pressure. Some embodiments further comprise: a wound dressing that comprises: a wound insert; and a drape configured to be coupled to skin adjacent a wound of a patient such that the drape covers the wound insert and the wound to form a space between the drape and the wound; In some embodiments, the wound insert comprises an open-celled hydrophilic foam. In some embodiments, the wound insert comprises a hydrophobic foam coated with a hydrophilic coating.

In some embodiments, the check-valve assembly comprises: a housing defining a first connection configured to be coupled to the wound dressing, a second connection configured to be coupled to the vacuum source, a first passageway between the first and second connections, and a second passageway between the first and second connections; a check valve disposed in the first passageway and configured to: permit fluid to pass through the check valve from the first connection to the second connection when the pressure at the second connection is less than the pressure at the first connection; and substantially prevent fluid from passing through the check valve from the second connection to the first connection when the pressure at the second connection is greater than the pressure at the first connection.

Some embodiments of the present wound-treatment methods comprise: applying negative pressure through a check-valve assembly and wound dressing to a wound of a patient, the wound dressing coupled to skin adjacent the wound such that the wound dressing covers the wound to form a substantially enclosed space adjacent the wound; and delivering a fluid to the wound dressing; where the check-valve assembly is configured to: substantially prevent backflow of fluids through the check-valve assembly, and substantially prevent pressure in the space between the drape and the wound from exceeding atmospheric pressure. In some embodiments, the wound dressing comprises: a wound insert; and a drape coupled to skin adjacent the wound such that the drape covers the wound insert and the wound to form the substantially enclosed space between the drape and the wound.

In some embodiments, delivering a fluid comprises activating a fluid source that is coupled to the wound dressing. In some embodiments, applying negative pressure comprises activating a vacuum source that is coupled to the wound dressing. In some embodiments, the wound insert comprises hydrophilic foam. In some embodiments, the wound insert comprises a hydrophobic foam coated with a hydrophilic coating. In some embodiments, the check-valve assembly comprises: a housing defining a first connection configured to be coupled to the wound dressing, a second connection configured to be coupled to the vacuum source, a first passageway between the first and second connections, and a second passageway between the first and second connections; a check valve disposed in the first passageway and configured to: permit fluid to pass through the check valve from the first connection to the second connection when the pressure at the second connection is less than the pressure at the first connection; and substantially prevent fluid from passing through the check valve from the second connection to the first connection when the pressure at the second connection is greater than the pressure at the first connection.

Some embodiments of the present wound-treatment methods comprise: coupling a wound dressing to skin adjacent a wound of a patient such that the wound dressing covers the wound to form a substantially enclosed space adjacent the wound; coupling the wound dressing to a fluid source such that the fluid source is actuatable to deliver fluid to the wound dressing; coupling the wound dressing to a check-valve assembly and a vacuum source such that the check-valve assembly: substantially prevents backflow of fluids through the check-valve assembly. Some embodiments comprise configuring the system such that the check-valve assembly also substantially prevents pressure in the space adjacent the wound from exceeding atmospheric pressure. In some embodiments, the wound dressing comprises: a wound insert comprising an open-celled foam configured to exhibit hydrophilic properties; and a drape; and where coupling the wound dressing comprises: positioning the wound insert on the wound; and coupling the drape to skin adjacent the wound such that the drape covers the wound insert and the wound, and forms a space between the drape and the wound. Some embodiments further comprise: applying a negative pressure to the wound through the check-valve assembly and the wound dressing; and delivering a fluid to the wound through the wound dressing. In some embodiments, the wound insert comprises hydrophilic foam. In some embodiments, the wound insert comprises a hydrophobic foam coated with a hydrophilic coating.

Any embodiment of any of the present systems and/or methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers.

FIG. 1 depicts a side view of one embodiment of the present wound dressings having one of the present wound inserts and coupled to a wound site and to a wound treatment apparatus.

FIG. 2A depicts an enlarged side view of the wound insert of FIG. 1.

DESCRIPTION OF ILLUSTRATIVE EMBODIMENTS

Figure 2B:
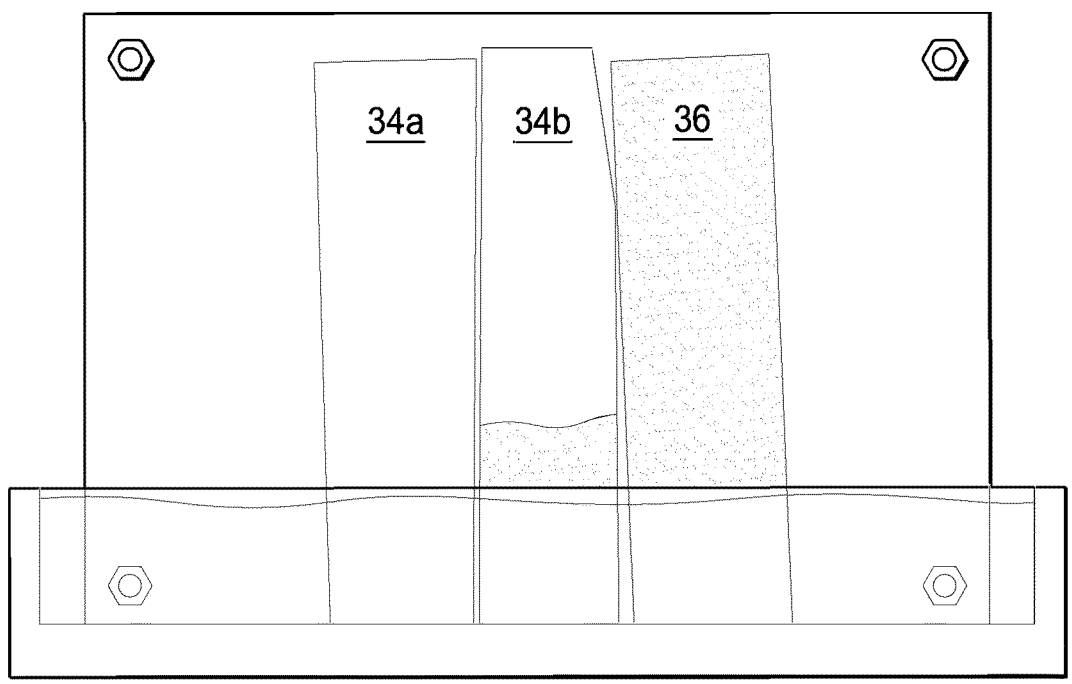
FIGS. 2B and 2C depict photographs showing experimental comparisons of fluid interaction of hydrophilic wound inserts relative to that of a prior hydrophobic wound insert.

The term "coupled" is defined as connected, although not necessarily directly, and not necessarily mechanically; two items that are "coupled" may be integral with each other. The terms "a" and "an" are defined as one or more unless this disclosure explicitly requires otherwise. The terms "substantially," "approximately," and "about" are defined as largely but not necessarily wholly what is specified, as understood by a person of ordinary skill in the art.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a method that "comprises," "has," "includes" or "contains" one or more steps possesses those one or more steps, but is not limited to possessing only those one or more steps. Likewise, a wound dressing that "comprises," "has," "includes" or "contains" one or more elements possesses those one or more elements, but is not limited to possessing only those elements. For example, in a wound dressing that comprises a wound insert and a drape, the wound dressing includes the specified elements but is not limited to having only those elements. For example, such a wound dressing could also include a connection pad.

Further, a device or structure that is configured in a certain way is configured in at least that way, but it can also be configured in other ways than those specifically described.

Referring now to the drawings, and more particularly to FIG. 1, shown therein is an embodiment of one of the present wound treatment system 10. In the embodiment shown, apparatus 10 comprises a wound-treatment apparatus 14, and a wound dressing 18 coupled to apparatus 14 by a conduit 22. As shown, dressing 18 is configured to be coupled to (and is shown coupled to) a wound 26 of a patient 30. More particularly, in the embodiment shown, dressing 18 comprises a wound insert 34 and a drape 38. As shown, wound insert 34 is configured to be positioned (and is shown positioned) on wound 26 (e.g., on or adjacent to wound surface 42), and/or drape 38 is configured to be coupled to (and is shown coupled to) skin 46 of the patient adjacent to wound 26 such that drape 38 covers wound insert 34 and wound 26, and forms a space 50 between drape 38 and wound 26 (e.g., wound surface 42).

Apparatus 14 can comprise, for example, a vacuum source configured to be actuatable (and/or actuated) to apply negative pressure (e.g., via conduit 22) to wound dressing 18, a fluid source configured to be actuatable (and/or actuated) to deliver (e.g., via conduit 22) a fluid (e.g., an installation fluid such as a medicinal fluid, antibacterial fluid, irrigation fluid, and or the like) to wound dressing 18. System 10 can be implemented and/or actuated and/or coupled to patient 30 in any of various configurations and/or methods similar to those described in the prior art. For example, various wound therapy systems and components are commercially available through and/or from KCI USA, Inc. of San Antonio, Tex., U.S.A.

Conduit 22 can comprise a single lumen conduit (e.g., switched between a vacuum source and/or a fluid source and apparatus 14), or can comprise multiple single-lumen conduits or a multi-lumen conduit such that, for example, fluid can be delivered and/or negative pressure can be applied to wound dressing 18 individually and/or simultaneously. Additionally, conduit 22 can comprise, for example, a first lumen for the application of negative pressure and/or fluid delivery, and at least one additional lumen for coupling to pressure sensor(s) to sense pressure (absolute pressure) or negative pressure (relative to atmospheric pressure) between drape 38 and surface 42. In some embodiments, conduit 22 can comprise multiple lumens (e.g., as in a single conduit with a central lumen for application of negative pressure and/or fluid delivery, and one or more peripheral lumens disposed adjacent or around the central lumen such that the peripheral lumens can be coupled to a pressure sensor to sense a pressure or negative pressure between drape 38 and surface 42 (e.g. in space 50). The lumens may be arranged with a central lumen and other lumens disposed radially around the central lumen, or in other suitable arrangements. The lumens may also be provided in separate conduits. In the embodiment shown, system 10 further comprises a wound dressing connection pad 54 configured to be coupled (and is shown coupled) to conduit 22. One example of a suitable connection pad 54 is the "V.A.C. T.R.A.C.® Pad," commercially available from KCI. One example of a suitable drape 38 includes the "V.A.C.® Drape" commercially available from KCI. Another example of a connection pad 54 is disclosed in U.S. patent application Ser. No. 11/702,822, published as Pub. No. US 2007/0219512 A1.

One example of a suitable drape 38 includes the "V.A.C.® Drape" commercially available from KCI USA, Inc. (and its affiliates) of San Antonio, Tex., U.S.A.

Referring now to FIG. 2A, a side view of wound insert 34 is shown. Wound insert 34 has an upper side 100, a lower side 104, lateral sides 108, 112, and interior volume 116. Although only one side is shown of wound insert 34, it will be understood by those of ordinary skill in the art that wound insert 34 includes a three-dimensional rectangular volume having a depth extending perpendicular to the side shown. In other embodiments, wound insert 34 can have any suitable shape, such as, for example, a round cylindrical shape, a fanciful shape, or may be trimmed to fit an irregular shape of a wound (e.g., 26 and/or wound surface 42).

The present embodiments of wound insert 34 comprise a foam (e.g., an open-celled foam, which may also be reticulated) that is configured to exhibit hydrophilic properties. In contrast to hydrophobic foams traditionally used with NPWT systems and methods, the hydrophilic properties of wound insert 34 provide improved movement of fluid (e.g., liquids such as instillation fluids, body fluids, exudate, and the like) through the wound insert, such that fluid is encouraged to travel through wound insert 34 rather than around the wound insert 34 or adjacent to the interface between drape 38 and skin 46.

With traditional hydrophobic wound inserts, fluid typically travels in a path such that the fluid minimizes contact with the foam, and such that fluid is repelled from the foam and may generate pressure between the foam and interface between drape 38 and skin 46. As such, hydrophobic wound inserts may force drape 38 away from skin 46 about the perimeter of wound 26. More particularly, with traditional hydrophobic wound inserts, very little of the fluid is retained or transferred through the foam itself. Because fluid may be forced outward from the hydrophobic wound insert, the fluid can generate a positive pressure (in excess of atmospheric pressure) at the interface between the drape and skin adjacent to the wound. This can lead to a ballooning effect which can stress the interface between the drape and the adjacent skin, and can lead to failure of the adhesive generally used to couple the drape to the skin. The ballooning effect can be particularly problematic if negative pressure is applied cyclically (e.g., on and off) and if fluids are introduced into the wound (e.g., instillation therapy).

However, with the present hydrophilic wound inserts 34, fluid can travel through or in at least a portion of wound insert 34 (e.g., evenly dispersed throughout wound insert 34), thus decreasing the positive pressure within the space 50 and at the interface between drape 38 and skin 46. As such, with the present hydrophilic wound inserts 34, fluid typically will not reach the interface between drape 38 and skin 46 as quickly, such that the integrity of adhesive or the like coupling drape 38 to skin 46 is maintained longer and permits more durable adhesion between drape 38 and skin 46. In this way, wound dressings 18 comprising drape 38 and wound insert 34 are typically more durable and/or less prone to failure.

As illustrated in FIG. 1, embodiments of the present wound dressings 18 comprise a wound insert 34 configured to be positioned on a wound 26 (e.g., wound surface 42) of a patient (e.g., 30), the wound insert comprising a foam (e.g., an open-celled foam, which may also be reticulated) configured to exhibit hydrophilic properties; and a drape 38 configured to be coupled to skin 46 of the patient adjacent the wound such that drape 38 covers wound insert 34 and wound 26 and forms a space 50 between the drape and the wound. Wound insert 34 can comprise any suitable material and/or combination of materials that permit wound insert 34 to exhibit hydrophilic properties. For example, in some embodiments, wound insert 34 comprises an open-celled hydrophobic foam that is coated with a hydrophilic coating (e.g., a coating configured to cause the hydrophobic foam to exhibit hydrophilic properties). In some embodiments, the hydrophilic coating comprises polyvinyl alcohol (PVOH), plasticizer (e.g., triethyl citrate, or the like), hydrophilic polyurethane, gelatin, hyaluronic acid, heparin, and/or any other suitable coating configured to cause the coated hydrophobic foam to exhibit hydrophilic properties.

Embodiments of the present methods of forming wound insert 34 comprise: applying a hydrophilic coating to an open-celled (which may also be reticulated) hydrophobic foam, where the coating is configured to cause the foam to exhibit hydrophilic properties. In some embodiments, the hydrophilic coating comprises polyvinyl alcohol (PVOH), plasticizer (e.g., triethyl citrate, or the like), hydrophilic polyurethane, gelatin, hyaluronic acid, heparin, and/or any other suitable coating configured to cause the coated hydrophobic foam to exhibit hydrophilic properties. In such embodiments, the coating can comprise a fluid coating, such as those that may be applied to a foam in a liquid state and dried, cross-linked, and/or otherwise cured to coat the foam (e.g., such that the coating is stable on the foam even in the presence of a fluid or liquid).

Figure 2C:
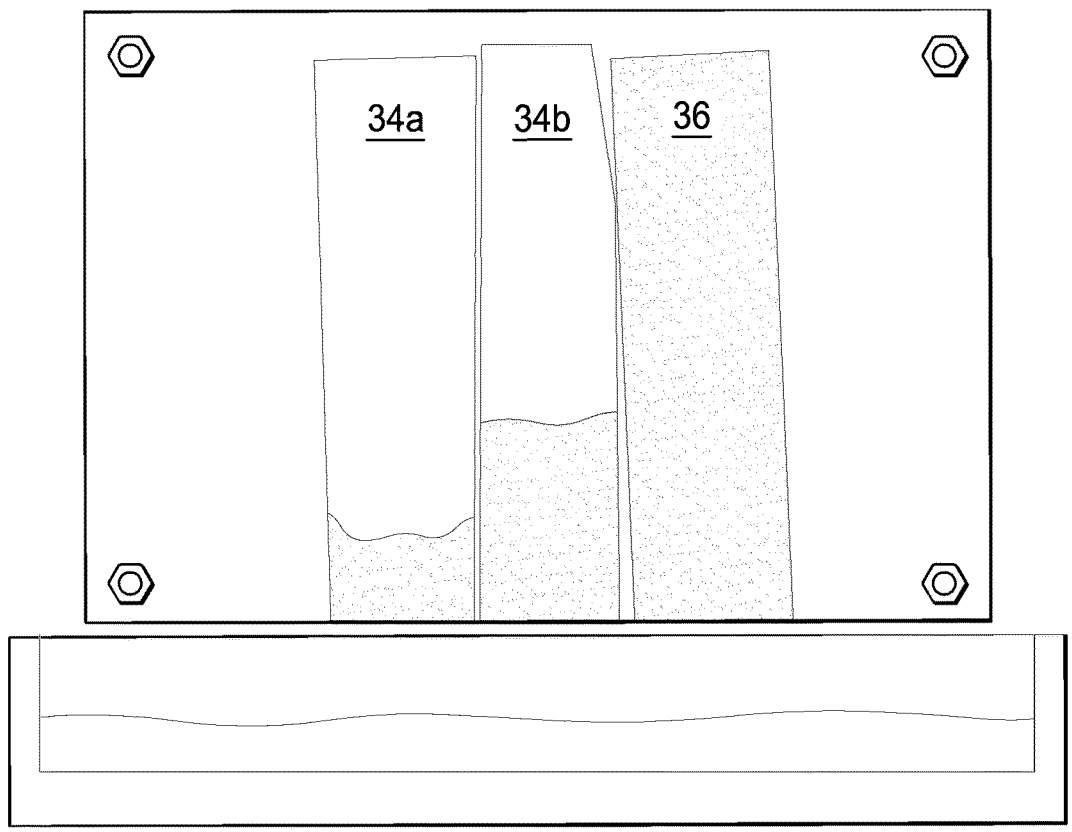

Referring now to FIGS. 2B and 2C, embodiments of the present wound inserts 34a and 34b are shown adjacent to a prior hydrophobic wound insert 36. In FIG. 2B, wound inserts 34a, 34b, and 36 are shown with a lower end disposed in a fluid. Wound insert 34a comprises a hydrophobic foam coated with a hydrophilic coating. Wound insert 34b comprises a hydrophilic foam. In FIG. 2C, wound inserts 34a, 34b, and 36 are shown removed from the fluid such that the dispersion of fluid in each of the wound inserts can be seen relative to one another. As shown, hydrophilic foam wound inserts 34a and 34b permit fluid to traverse upward and disperse throughout wound inserts 34a and 34b. In contrast, hydrophobic wound insert 36 expands and substantially repels the fluid from traversing, entering, or otherwise becoming dispersed throughout wound insert 36. In this way, wound insert 36 effectively forces fluid to the edges of wound insert 36 such that if wound insert 36 is used in a wound dressing 18, the fluid that is repelled from wound insert 36 can exert an outward force on the interface between drape 38 and skin 46, and/or can infiltrate the adhesive between drape 38 and skin 46, as described above. In contrast, and as illustrated in FIGS. 2B and 2C, hydrophilic foam wound inserts 34a and 34b permit fluid to traverse wound inserts 34a and 34b to substantially prevent and/or reduce outward forces on drape 38 (e.g., caused by positive pressure between drape 38 and wound 30), and/or fluid infiltration of adhesive between drape 38 and skin 46.

Figure 3:
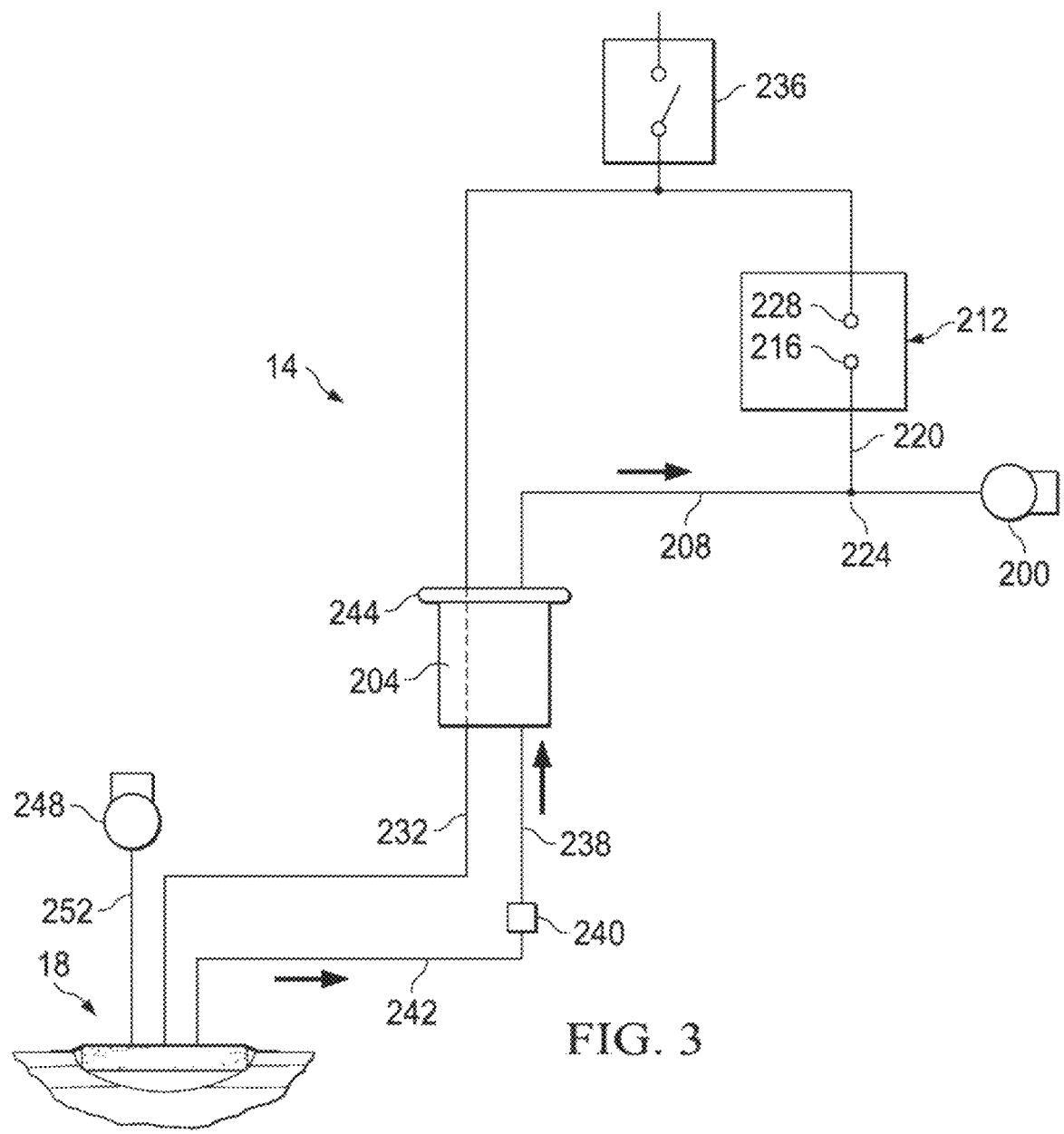
FIG. 3 depicts a schematic block diagram of one embodiment of a wound treatment apparatus that can comprise and/or be coupled to and/or be used with the present wound dressings and/or wound inserts.

Embodiments of the present wound treatment methods may be better understood with reference to FIG. 3. FIG. 3 depicts the schematic block diagram of one embodiment of system 10. In the embodiment shown, wound dressing 18 is coupled to apparatus 14, and apparatus 14 comprises a vacuum source 200 (e.g., a vacuum pump and/or the like) coupled to a canister 204 (e.g., configured to receive exudate and or the like from wound dressing 18) by way of a conduit 208. In the embodiment shown, apparatus 14 further comprises: a pressure sensor 212 having a first pressure transducer 216 coupled to conduit 208 by way of conduit 220 and/or tee-fitting 224, and a second pressure transducer 228 coupled to canister 204 and/or wound dressing 18 by way of conduit 232. Pressure sensor 212 is configured to sense the negative pressure in wound dressing 18 and/or any of the various conduits coupled to wound dressing 18, pressure sensor 212, and/or vacuum source 200.

In the embodiment shown, apparatus 14 further comprises a pressure release valve 236 coupled to conduit 232. Further, in the embodiment shown, canister 204 and vacuum source 200 are coupled to wound dressing 18 by way of a conduit 238, a check-valve assembly 240 (which may also be referred to as a one-way valve assembly 240), and a conduit 242. More particularly, conduit 238 couples canister 204 to check-valve assembly 240, and conduit 242 couples check-valve assembly 240 to wound dressing 18. In the embodiment shown, canister 204 comprises a filter 244 at or near an outlet of canister 204 to prevent liquid or solid particles from entering conduit 208. Filter 244 can comprise, for example, a bacterial filter that is hydrophobic and/or lipophilic such that aqueous and/or oily liquids will bead on the surface of the filter. Apparatus 14 can be configured such that during operation of vacuum source 200 will provide sufficient airflow through a filter 244 that the pressure drop across filter 244 is not substantial (e.g., such that the pressure drop will not substantially interfere with the application of negative pressure to wound dressing 18 from vacuum source 200).

In various embodiments, such as the one shown in FIG. 3, apparatus 14 can be configured such that as soon as liquid in the canister reaches a level where filter 244 is occluded, a much-increased negative (or subatmospheric) pressure occurs in conduit 208 and is sensed by transducer 216. Transducer 216 can be connected to circuitry that interprets such a pressure change as a filled canister and signals this by means of a message on an LCD and/or buzzer that canister 204 requires emptying and/or replacement, and/or that automatically shuts off or disables vacuum source 200.

Apparatus 14 can also be configured to apply intermittent negative (or subatmospheric) pressure to the wound site, and/or such that pressure relief valve 236 enables pressure at the wound site to be brought to atmospheric pressure rapidly. Thus, if apparatus 14 is programmed, for example, to relieve pressure at ten-minute intervals, at these intervals pressure relief valve 236 can open for a specified period, allow the pressure to equalize at the wound site, and then close to restore the negative pressure. It will be appreciated that when constant negative pressure is being applied to the wound site, valve 236 remains closed to prevent leakage to or from the atmosphere. In this state, it is possible to maintain negative pressure at the wound site without running and/or operating pump 200 continuously, but only from time to time or periodically, to maintain a desired level of negative pressure (i.e. a desired pressure below atmospheric pressure), which is sensed by transducer 216. This saves power and enables the appliance to operate for long periods on its battery power supply.

In the embodiment shown, apparatus 14 further comprises a fluid source 248 coupled to wound dressing 18 by way of a conduit 252 such that such that fluid source 248 is actuatable to deliver a fluid to wound dressing 18 (e.g., to the wound through the wound dressing). Fluid source 248 can be any suitable mechanism capable of delivering fluid, such as, for example, a syringe, a fluid pump, and/or the like. Typically, in systems such as apparatus 14 that do not have a check-valve assembly, before fluid is delivered to the wound dressing, the wound dressing (e.g., the space in the wound dressing) is returned to atmospheric pressure, and the conduit (e.g., conduit 238) between the wound dressing and the canister is clamped to prevent backflow of fluids of fluids through the check-valve assembly. This can lead to leakage and/or rupture of the adhesive boundary between the wound dressing 18 and the skin of the patient, because as fluid is delivered to the sealed (or substantially sealed) environment within the wound dressing, it can pressurize the wound dressing and/or force fluids to the boundary of the wound dressing.

However, in the embodiment shown, check-valve assembly 240 is configured to substantially prevent (prevent up to all, but may be subject to some leakage, such as during transition between open and closed configurations, as described in this disclosure) backflow (flow back towards wound dressing 18) of fluids through check-valve assembly 240 (e.g., from conduit 238 to conduit 242) and/or into wound dressing 18; and to substantially prevent pressure in the space adjacent the wound (e.g., within wound dressing 18) from exceeding atmospheric pressure, such as when pressure release valve 236 is opened to prevent canister 204 from exceeding atmospheric pressure (or if canister 204 is otherwise vented to prevent conduit 238 from exceeding atmospheric pressure). It should be appreciated that some backflow may occur from conduit 242 into wound dressing, but will be substantially prevented upstream of check-valve assembly 240 (e.g., from conduit 238). In some embodiments, backflow from conduit 242 is minimized by placing or disposing check-valve assembly 240 adjacent to wound dressing 18 (e.g., within 1, 2, 3, 4, 5, 6, 7, 8, 9, 10, 11, 12, 13, 14, 15, 16, 17, 18, 19, or 20 cm of wound dressing 18) and/or making check-valve assembly 240 a part of wound dressing 18 (e.g., such that check valve assembly 240 is disposable with wound dressing 18). For example, in some embodiments, check-valve assembly 240 is disposed within 5 cm or less of wound dressing 18 such that the volume is minimized within conduit 242 between check-valve assembly 240 and wound dressing 18.

In the embodiment shown, negative pressure (a pressure below atmospheric pressure) in the wound dressing 18 can be maintained (e.g., the wound dressing 18 need not be returned to atmospheric pressure) prior to delivering fluid to the wound dressing, such that backflow is substantially prevented through the check-valve assembly 240 into wound dressing 18, and such that as pressure in wound-dressing 18 increases to the pressure in conduit 238, check-valve assembly will permit the flow of fluids (and the release of pressure) from one side of the check-valve assembly to the other (e.g., from wound dressing 18 and conduit 242, through check-valve assembly 240, to conduit 238). In this way, check-valve assembly 240 is configured to maintain negative pressure at wound dressing 18 prior to instillation therapy (delivery of fluid to the wound dressing), thereby minimizing liquid leaks caused from ballooning and/or failure of the drape adhesive, and to minimize the amount of fluid that is wasted. For example, during normal operation, negative pressure can be maintained for a period of time at the wound dressing, and atmospheric pressure can be introduced at the canister (e.g., by venting canister 204 to atmosphere to cause the pressure in canister 204 to increase to atmospheric pressure (with the corresponding decrease in "negative pressure")). As fluid is metered into the wound dressing, the pressure at the wound site will increase until it reaches atmospheric pressure. Once the pressure in wound dressing 18 (and conduit 242) reaches or exceeds the pressure in conduit 238 (and canister 204), check-valve assembly 240 will permit flow across the check-valve assembly from conduit 242 to conduit 238, and thereby prevent the wound dressing from overfilling.

Figure 4:
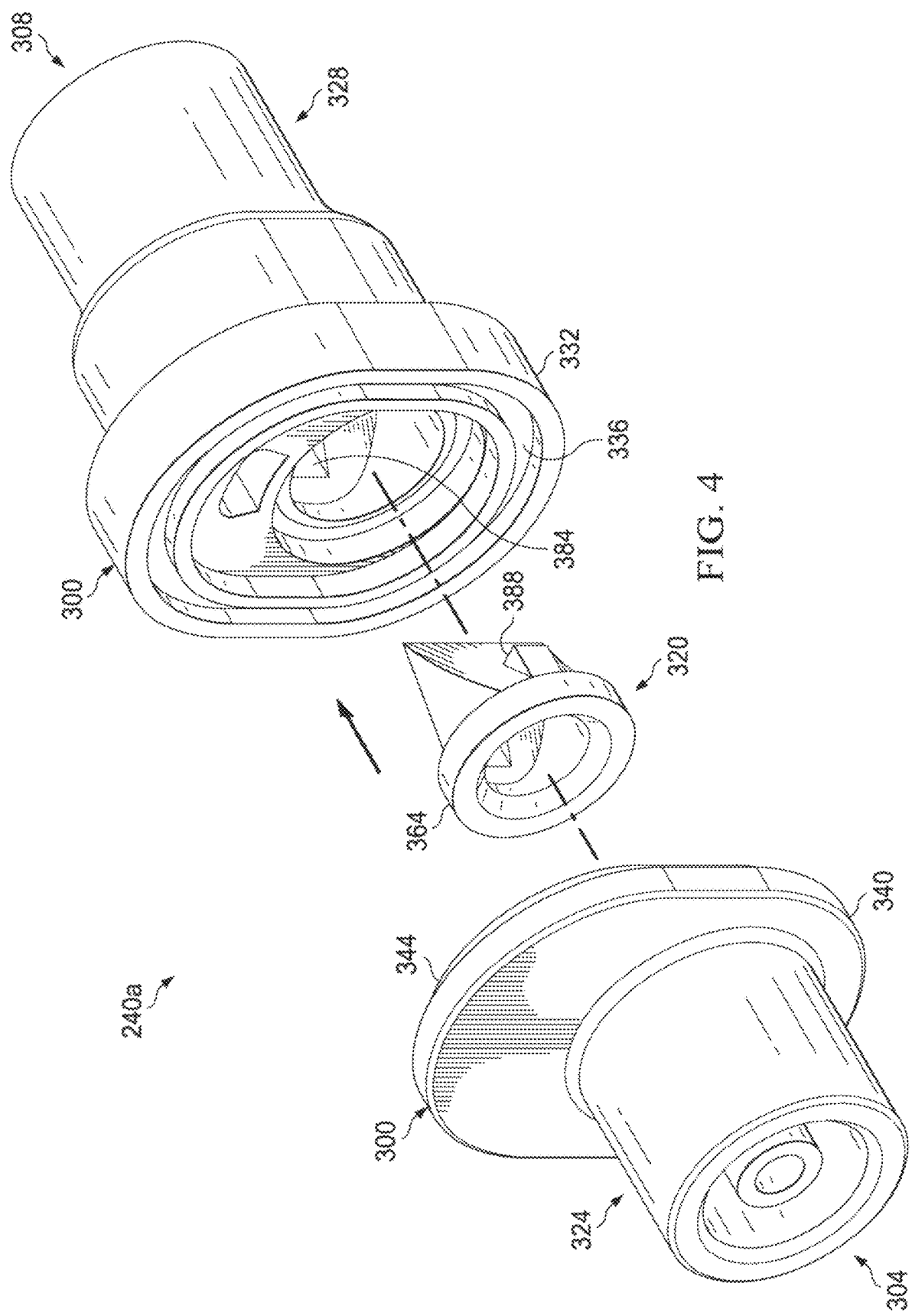
FIG. 4 depicts a perspective view of one of the present check-valve assemblies.
Figure 5:
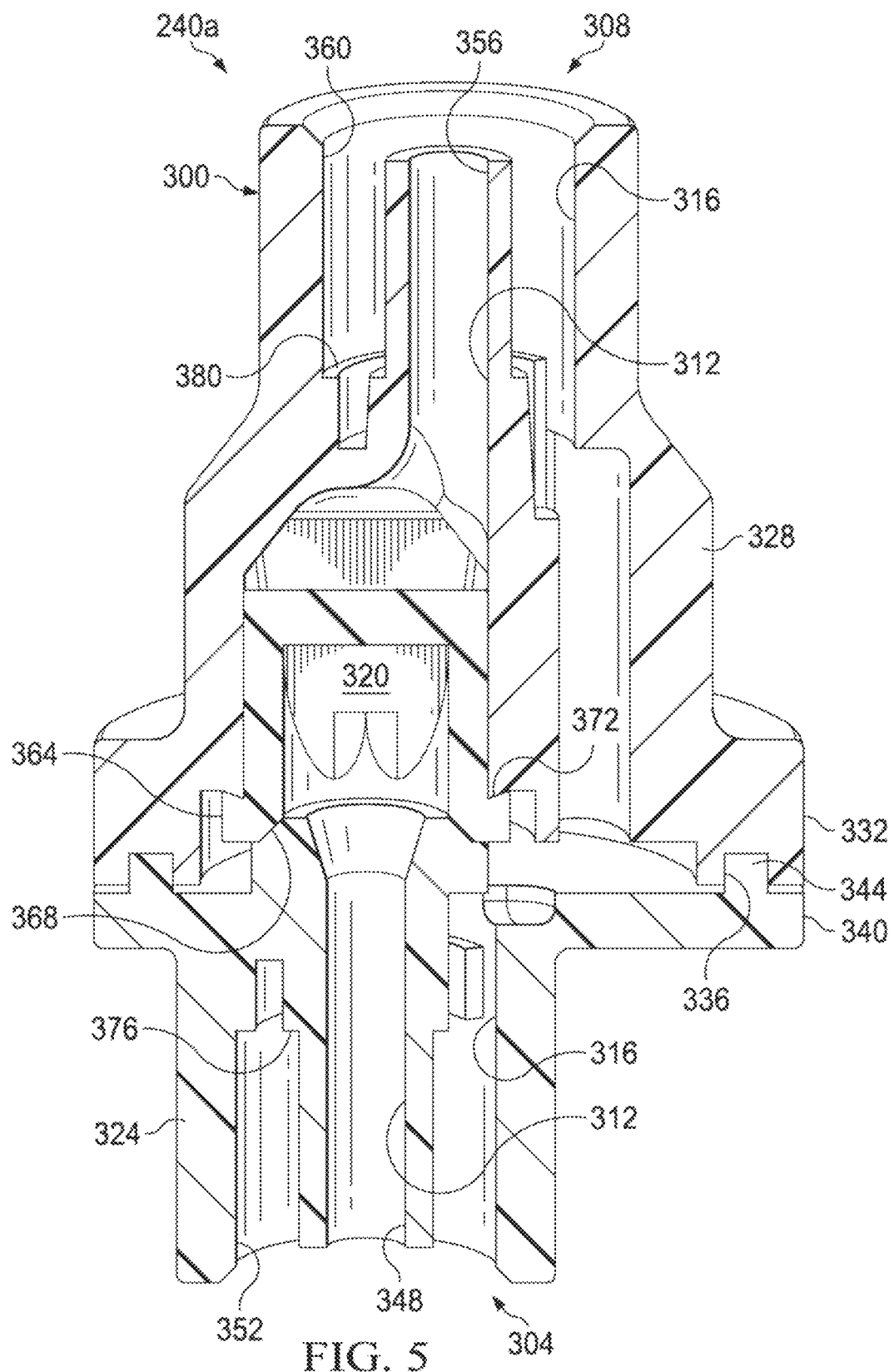
FIG. 5 depicts a cross-sectional side view of the check-valve assembly of FIG. 4.
Figure 6:
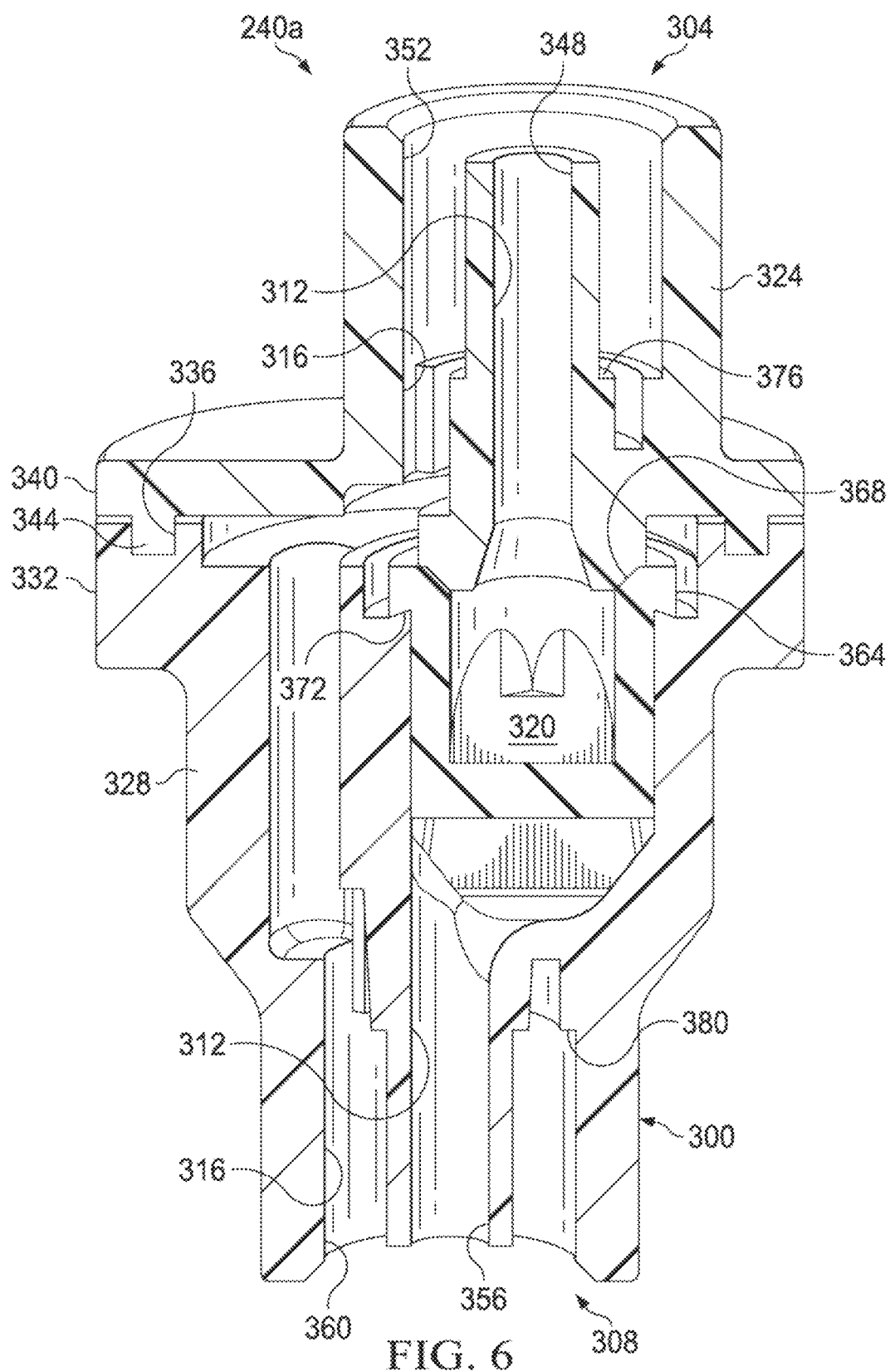
FIG. 6 depicts a cross-sectional side view of the check-valve assembly of FIG. 4.

Referring now to FIGS. 4-6, an embodiment 240*a* is shown of the present check-valve assemblies. More particularly, FIG. 4 depicts a perspective view of check-valve assembly 240*a*; FIG. 5 depicts a cross-sectional side view of check-valve assembly 240*a*; and FIG. 6 depicts a cross-sectional side view of check-valve assembly 240*a*. In the embodiment shown, check-valve assembly 240*a* comprises: a housing 300 defining a first connection 304, and a second connection 308. Housing 300 further defines a first passageway 312 between first and second connections 304 and 308, and a second passageway 316 between first and second connections 304 and 308. As shown, second passageway 316 is distinct from (e.g., separate from and not in fluid communication with) first passageway 312. In the embodiment shown, check-valve assembly 240*a* further comprises a check valve 320 disposed in first passageway 312, and configured to: permit fluid to pass through check valve 320 (e.g., through first passageway 312) from first connection 304 to second connection 308 if the pressure at second connection 308 is less than the pressure at first connection 304. In the embodiment shown, check valve 320 is further configured to substantially prevent (prevent up to all, but may be subject to some leakage, such as during transition between open and closed configurations, as described in this disclosure) fluid from passing through check valve 320 from first connection 304 to second connection 308 if the pressure at second connection 308 is greater than the pressure at first connection 304. For example, in the apparatus of FIG. 3, first connection 304 of check-valve assembly 240*a* would be coupled to conduit 242, and second connection 308 would be coupled to conduit 238.

In the embodiment shown, housing 300 comprises a first member 324 and a second member 328 configured to be coupled to one another by any suitable structure or method, such as, for example, with interlocking tabs, adhesive, screws, rivets, ultrasonic welding, thermal welding, or the like. In the embodiment shown, second member 328 has a coupling end 332 (e.g., opposing second connection 308) having a groove 336 (e.g., a peripheral groove, as shown), and first member 324 has a coupling end 340 (e.g., opposing first connection 304) having a ridge 344 (e.g., a peripheral ridge, as shown) configured to extend into groove 336 when the first and second members 324 and 328 are coupled to one another, as shown in FIGS. 5 and 6, such that ridge 344 and groove 336 cooperate to improve the connection (e.g., the strength and/or integrity of the connection) between first and second members 324 and 328. In the embodiment shown, first and second members 324 and 328 are configured to be coupled to one another with adhesive and/or by ultrasonic welding. As shown, first and second members 324 and 328 cooperate to define first and second passageways 312 and 316, and/or check valve 320 cooperates with first and second members 324 and 328 to seal between first and second housings 324 and 328 such that first passageway 312 is distinct from second passageway 316 (e.g., fluid communication is substantially prevented between first and second passageways 312 and 316).

In the embodiment shown, first connection 304 comprises a multi-lumen connection having a first lumen 348 in communication with first passageway 312, and a second lumen 352 in communication with second passageway 316. Additionally, in the embodiment shown, second connection 308 comprises a multi-lumen connection having a first lumen 356 in communication with first passageway 312, and a second lumen 360 in communication with second passageway 316. More particularly, in the embodiment shown, second lumen 352 of first connection 304 is an annular lumen disposed around first lumen 348 of first connection 304; and second lumen 360 of second connection 308 is an annular lumen disposed around first lumen 356 of second connection 308.

In the embodiment shown, check valve 320 is a duckbill valve. In the embodiment shown, valve 320 comprises an enlarged base portion 364 configured to fit around the perimeter of first passageway 312 in housing 300. Additionally, first and second members 324 and 328 (and/or enlarged base portion 364) are configured such that when valve 320 is disposed in first passageway 312, and first and second members 324 and 328 are coupled to one another, as shown in FIGS. 5 and 6, the first and second members compress at least a portion of enlarged base portion 364 to provide a seal between first and second members 324 and 328 and to substantially prevent fluid communication between first and second passageways 312 and 316 within housing 300. More particularly, in the embodiment shown, first member 324 comprises a circular protrusion 368 having an angled or chamfered outer edge; and second member 328 comprises an angled ledge 372. Protrusion 368 and ledge 372 are configured such that when valve 320 is disposed in first passageway 312, and first and second members 324 and 328 are coupled to one another: protrusion 368 extends into the middle of and presses against and inner surface of enlarged base portion 364, and ledge 372 presses against an outer surface of enlarged base portion 364, such that protrusion 368 and ledge 372 cooperate to compress enlarged base portion 364 around the perimeter of first passageway 312, as shown in FIGS. 5 and 6.

In the embodiment shown, the multi-lumen configuration of first and second connections permits check-valve assembly 240a to be coupled to a multi-lumen conduit (e.g., a multi-lumen PVC tubing) between a wound dressing (e.g., 18) and an apparatus comprising a vacuum source (e.g., 200) and a pressure sensor (e.g., pressure transducer 212). For example, some commercially available NPWT apparatuses are configured to combine the vacuum or negative pressure conduit (e.g., 240, 242) and the pressure-sensor conduit (e.g., 232) into a single multi-lumen conduit (not shown), such that the pressure-sensor conduit comprises a plurality of peripheral lumens disposed around a central vacuum or negative pressure lumen in the multi-lumen conduit. To ensure communication between peripheral pressure-sensor lumens, first member 324 includes a shelf 376 in annular lumen 352, and second member 328 includes a shelf 380 in annular lumen 360, to prevent the peripheral pressure lumens in a multi-lumen tube from being blocked by first member 324, such that communication is permitted between the peripheral pressure-sensor lumens and the second passageway 316.

In the embodiment shown, second member 328 comprises indents 384 (two indents 384 on opposite sides of first passageway 312), and check valve 320 comprises protrusions 388 (two protrusions 388 on opposite sides of valve 320) that correspond to indents 384, such that indents 384 and protrusions 388 cooperate to orient valve 320 in body 300 and/or to prevent rotation of valve 320 in body 300. Although valve 320 is shown as a duckbill valve, in other embodiments check valve 320 can comprise a ball valve or an umbrella valve.

Some embodiments of the present wound-treatment methods comprise: applying negative pressure through a check-valve assembly (e.g., 240, 240a) and wound dressing (e.g., 18) to a wound (e.g., 26) of a patient (e.g., 30), the wound dressing coupled to skin (e.g., 46) adjacent the wound such that the wound dressing covers the wound to form a substantially enclosed space (e.g., 50) adjacent the wound. Some embodiments comprise delivering a fluid to the wound dressing (e.g., from a fluid source 248). In some embodiments, the check-valve assembly is configured to: substantially prevent backflow of fluids through the check-valve assembly, and substantially prevent pressure in the space between the drape and the wound from exceeding atmospheric pressure. In some embodiments, delivering a fluid comprises activating a fluid source (e.g., 248) that is coupled to the wound dressing. In some embodiments, applying negative pressure comprises activating a vacuum source (e.g., 200) that is coupled to the wound dressing.

Some embodiments of the present wound-treatment methods comprise: coupling a wound dressing (e.g., 18) to skin (e.g., 46) adjacent a wound (e.g., 26) of a patient (e.g., 30) such that the wound dressing covers the wound to form a substantially enclosed space (e.g., 50) adjacent the wound. Some embodiments comprise: coupling the wound dressing to a fluid source (e.g., 248) such that the fluid source is actuatable to deliver fluid to the wound dressing. Some embodiments comprise: coupling the wound dressing to a check-valve assembly (e.g., 240, 240a) and a vacuum source (e.g., 200) such that the check-valve assembly: substantially prevents backflow of fluids through the check-valve assembly. In some embodiments, the system can be configured such that the check-valve assembly substantially prevents pressure in the space adjacent the wound from exceeding atmospheric pressure, such as when pressure release valve 236 is opened to prevent canister 204 from exceeding atmospheric pressure (or if canister 204 is otherwise vented to prevent conduit 238 from exceeding atmospheric pressure). In some embodiments, the wound dressing comprises a wound insert (e.g., 34) and a drape (e.g., 38), and coupling the wound dressing comprises: positioning the wound insert on the wound; and coupling the drape to skin adjacent the wound such that the drape covers the wound insert and the wound, and forms a space between the drape and the wound. Some embodiments comprise: applying a negative pressure to the wound through the check-valve assembly and the wound dressing; and delivering a fluid to the wound through the wound dressing.

Embodiments of any of the present methods can utilize, include the use of, and/or otherwise comprise any of the apparatuses, wound dressings, wound inserts, and/or check-valve assemblies described in this disclosure. In any of the present wound-treatment methods, fluid can be delivered to the wound dressing 18 prior to applying negative pressure to wound dressing 18, negative pressure can be applied to wound dressing 18 prior to fluid being delivered to wound dressing 18, and/or fluid can be delivered wound dressing 18 simultaneously with negative pressure being applied to wound dressing 18.

In some embodiments of the present wound-treatment methods, a skin preparation can be used in combination with the present wound dressings 18 to improve the adhesion and durability of the interface between drape 38 and skin 46, such as, for example, to mitigate and/or reduce leaks. For example, skin 46 adjacent wound 26 can be cleaned and coated with a coating that is impervious and/or insoluble in water. In this way, adhesion between drape 28 and coated skin 46 can be improved and/or can be made more durable by reducing its susceptibility to infiltration from water-based installation fluids that may be delivered to wound dressing 18 and/or to space 50. By way of another example, a coating can be applied to the skin (e.g., in a manner similar to certain adhesives) that dries or sets into a layer on top of the skin that is durable enough to reduce and/or prevent maceration of the skin to reduce trauma to the underlying skin upon removal of the drape from the skin.

The present embodiments of the systems, methods, and when dressings reduce the risks associated with fluid instillation by delaying and/or minimizing fluid contact and/or infiltration of the interface between drape 38 and skin 46 that could degrade adhesive that is often used to couple drape 38 to skin 46 when wound dressing 18 is coupled to a patient 30. Additionally, improved fluid management can decrease the positive pressure that might otherwise be generated at the interface between drape 38 and skin 46 so as to reduce mechanical strains that would otherwise act to pull drape 38.

The various illustrative embodiments of devices, systems, and methods described herein are not intended to be limited to the particular forms disclosed. Rather, they include all modifications and alternatives falling within the scope of the claims.

The claims are not intended to include, and should not be interpreted to include, means-plus- or step-plus-function limitations, unless such a limitation is explicitly recited in a given claim using the phrase(s) "means for" or "step for," respectively.

It will be understood that the benefits and advantages described above may relate to one embodiment or may relate to several embodiments. It will further be understood that reference to 'an' item refers to one or more of those items, unless otherwise specified.

The steps of the methods described herein may be carried out in any suitable order, or simultaneously where appropriate.

Where appropriate, aspects of any of the examples described above may be combined with aspects of any of the other examples described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments. Although various embodiments have been described above with a certain degree of particularity, or with reference to one or more individual embodiments, those skilled in the art could make numerous alterations to the disclosed embodiments without departing from the scope of this invention.

The invention claimed is:

1. A wound-treatment method comprising:
  applying negative pressure through a check-valve assembly and wound dressing to a wound of a patient, the wound dressing coupled to skin adjacent the wound such that the wound dressing covers the wound to form a substantially enclosed space adjacent the wound; and
  delivering a fluid to the wound dressing;
  where the check-valve assembly comprises:
    a first member having a first connection configured to be fluidly coupled to the wound dressing that is fluidly coupled to a fluid source, a first lumen, and a second annular lumen disposed around the first lumen, wherein the first lumen and the second annular lumen extend from the first connection through the first member,
    a second member having a second connection configured to be fluidly coupled to a vacuum source, a first lumen, and a second annular lumen disposed around the first lumen, wherein the first lumen and the second annular lumen extend from the second connection through the second member,
    a check valve disposed in a passageway formed between the first lumens of the first and second member, and wherein the second annular lumens of the first and second member are fluidly coupled so that they are not in fluid communication with the first lumens of the first and second member and the passageway; and
  wherein the check-valve assembly is configured to:
    substantially prevent backflow of fluids through the check-valve assembly, and
    substantially prevent pressure in the space between the wound dressing and the wound from exceeding atmospheric pressure.

2. The method of claim 1, where the wound dressing comprises:
  a wound insert; and
  a drape coupled to skin adjacent the wound such that the drape covers the wound insert and the wound to form the substantially enclosed space between the drape and the wound.

3. The method of claim 1, where delivering a fluid comprises activating the fluid source that is coupled to the wound dressing.

4. The method of claim 1, where applying negative pressure comprises activating the vacuum source that is coupled to the wound dressing.

5. The method of claim 1, where the wound insert comprises hydrophilic foam.

6. The method of claim 1, where the wound insert comprises a hydrophobic foam coated with a hydrophilic coating.

7. A wound-treatment method comprising:
  coupling a wound dressing to skin adjacent a wound of a patient such that the wound dressing covers the wound to form a substantially enclosed space adjacent the wound;
  coupling the wound dressing to a fluid source such that the fluid source is actuatable to deliver fluid to the wound dressing;
  coupling the wound dressing to a check-valve assembly and a vacuum source such that the check-valve assembly substantially prevents backflow of fluids through the check-valve assembly, and comprises
    a first member having a first connection configured to be fluidly coupled to the wound dressing that is fluidly coupled to the fluid source, a first lumen, and a second annular lumen disposed around the first lumen, wherein the first lumen and the second annular lumen extend from the first connection through the first member,
    a second member having a second connection configured to be fluidly coupled to the vacuum source, a first lumen, and a second annular lumen disposed around the first lumen, wherein the first lumen and the second annular lumen extend from the second connection through the second member,
    a check valve disposed in a passageway formed between the first lumens of the first and second member, and wherein the second annular lumens of the first and second member are fluidly coupled so that they are not in fluid communication with the first lumens of the first and second member and the passageway.

8. The method of claim 7, further comprising:
configuring the system such that the check-valve assembly also substantially prevents pressure in the space adjacent the wound from exceeding atmospheric pressure.

9. The method of claim 7, where the wound dressing comprises:
a wound insert comprising an open-celled foam configured to exhibit hydrophilic properties; and
a drape; and
where coupling the wound dressing comprises:
positioning the wound insert on the wound; and
coupling the drape to skin adjacent the wound such that the drape covers the wound insert and the wound, and forms a space between the drape and the wound.

10. The method of claim 7, further comprising:
applying a negative pressure to the wound through the check-valve assembly and the wound dressing; and
delivering a fluid to the wound through the wound dressing.

11. The method of claim 7, where the wound insert comprises hydrophilic foam.

12. The method of claim 7, where the wound insert comprises a hydrophobic foam coated with a hydrophilic coating.

* * * * *